(12) United States Patent
Anantheswaran et al.

(10) Patent No.: US 6,422,063 B1
(45) Date of Patent: Jul. 23, 2002

(54) RAPID METHOD TO EXPERIMENTALLY MEASURE THE GAS PERMEABILITY OF MICRO-PERFORATED FILMS

(76) Inventors: Ramaswamy C. Anantheswaran, 638 Berkshire Dr.; Vikramaditya Ghosh, 600 E. Pollock Rd., both of State College, PA (US) 16801

( * ) Notice: Subject to any disclaimer, the term of this patent is extended or adjusted under 35 U.S.C. 154(b) by 0 days.

(21) Appl. No.: 09/371,630

(22) Filed: Aug. 11, 1999

Related U.S. Application Data

(60) Provisional application No. 60/096,067, filed on Aug. 11, 1998.

(51) Int. Cl.[7] .............................................. G01N 15/08
(52) U.S. Cl. ......................................................... 73/38
(58) Field of Search .............................................. 73/38

(56) References Cited

U.S. PATENT DOCUMENTS

| | | | | |
|---|---|---|---|---|
| 3,590,634 A | * | 7/1971 | Pasternak et al. | 73/38 |
| 4,246,775 A | * | 1/1981 | Stultz | 73/38 |
| 4,391,128 A | * | 7/1983 | McWhorter | 73/38 |
| 4,852,389 A | * | 8/1989 | Mayer et al. | 73/38 |
| 5,138,871 A | * | 8/1992 | Retta et al. | 73/38 |
| 5,646,335 A | * | 7/1997 | Wenman et al. | 73/38 |
| 5,679,885 A | * | 10/1997 | Lenormand et al. | 73/38 |
| 6,009,743 A | * | 1/2000 | Mayer | 73/38 |
| 6,324,898 B1 | * | 12/2001 | Cote et al. | 73/38 |
| 6,327,892 B1 | * | 12/2001 | Koiso et al. | 73/38 |

OTHER PUBLICATIONS

Renault et al., Gas Exhange in Modified Atmosphere Packaging, Pt. 1: A New Theoretical Approach for Micro–Performated Packs, Pt. 2: Experimental Results with Strawberries, 1994, Int'l Journal of Food Science and Technology 29 (4) p. 365–394.*

ASTM D 3985. 1995. Standard method for oxygen gas transmission rate through plastic film and sheeting using a coulometric sensor. *American Society for Testing Materials,* Philadelphia, PA. pp. 207–218.

ASTM D 1434. 1995. Standard test method for determining gas permeability characteristics of plastic films and sheeting. *American Society for Testing Materials,* Philadelphia, PA. pp. 534–539.

Brown, R. P. 1998. Permeability. In *Handbook of Plastic Test Methods.* Roger P. Brown (ed.) Longman Scientific and Technical, John Wiley and Sons, Inc., New York. pp. 387–402.

Emond, J. P., Castaigne, F., Toupin, C. J., and Desilets, D. 1991. Mathematical modeling of gases in modified atmosphere packaging. Trans. ASAE. 34 (1): 239–245.

Fishman, S., Rodov, V., and Ben–Yehoshua, S. 1996. Mathematical model for perforation effect on oxygen and water vapor transport dynamics in modified atmosphere packages. J. Food Science. 61 (5): 956–961.

Fonseca, S. C., Olivera, F. A. R., and Chau, K. V. 1996. Oxygen and carbon dioxide exchange through perforation for development of perforated modified atmosphere bulk packages. Poster presented in the IFT Annual Meeting, New Orleans, LA.

(List continued on next page.)

*Primary Examiner*—Hezron Williams
*Assistant Examiner*—C D Garber
(74) *Attorney, Agent, or Firm*—McKee, Voorhees & Sease, P.L.C.

(57) ABSTRACT

A workable setup for rapidly measuring the permeability of the micro-perforated films has been developed, using both static and flow-through methods. The static method simulates the normal package conditions and thus the data obtained can be used for designing modified atmosphere packages. The drawback with this method is that it takes a long time to give results, typically two days for one run and a week to run three replicates. The flow through method is very simple and less time consuming. It takes about two hours to get a set of readings and three replicates can be obtained in half a day. The drawback of the flow through method is that it gives a higher reading than the static method. A regression equation was obtained to get a correlation between the readings obtained by the flow through method and the static method ($R^2=93\%$). These methods can also be used to measure the carbon dioxide permeability.

41 Claims, 20 Drawing Sheets

OTHER PUBLICATIONS

Figure 1:
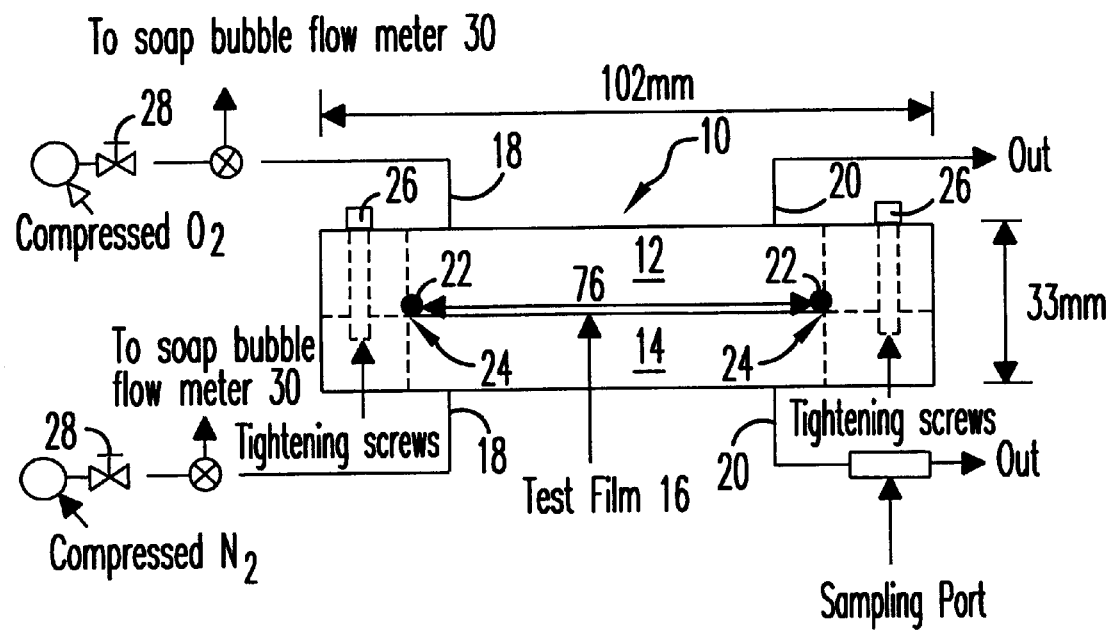

Gilbert, S. G. and Pegaz, D. 1969. Find new ways to measure gas permeability. Package engineering. pp. 66–69.

Hirata, T., Makino, Y., Ishikawa, Y., Katusara, S., and Hasegawa. 1996. A theoretical model for designing a modified atmosphere packaging with a perforation. Trans. ASAE. 39 (4): 1499–1504.

Johnson, B. and Demorest, R. 1997. Testing, permeation and leakage. In *The Wiley Encyclopedia of Packaging*. A. Brody and K. Marsh (eds.) John Wiley and Sons, Inc., New York, pp. 895–901.

Moyls, L., Hocking, R., Beveridge., and Timbers, G. 1992. Exponential decay method for determining gas transmission rate of films. Trans ASAE 35(4): 1259–1265.

Stannet, V. and Yasuda, H. 1965. The measurement of gas and vapor and diffusion in polymers. In *Testing of Polymers*, vol. 1. John V. Schmitz (ed.) Interscience Publishers. pp. 393–418.

Ghosh, V. 1998 Design of a setup for measuring the oxygen transmission rate of micro–perforated films. *Master Thesis*, Pennsylvania State University, pp. i–ix; 1–122.

* cited by examiner

| Model | Reference |
|---|---|
| $Q = \dfrac{D_{AB} P A}{RTL\alpha} \ln\left[\dfrac{1-\alpha y_{AL}}{1-\alpha y_{AO}}\right]$ <br><br> A is the area of the film (m²) | Youngquist (1970) |
| The L in model 1 is modified as: <br> $L = x + R_h$, where $R_h$ is the radius of the perforation and, x is the film thickness. | Fishman et al. (1996) |
| $Q = \dfrac{A(p_2 - p_1)}{\sqrt{2\pi MRT}}$ <br><br> M = molecular weight of the gas (kg mmol⁻¹) <br> T = temperature, K. <br> R = universal gas constant | Hirata et al. (1996) |
| $Q = A(a_1 + a_2(dp)^2 + a_3(Ep) + a_4(T) + a_5(dp)^4 + a_6(Ep)^2 + a_7(T)^2 + a_8(dp)^2(Ep) + a_9(dp)^2(T) + a_{10}(Ep)(T)$ <br><br> where dp is the diameter of the perforation, Ep is the thickness of the perforation, T is the temperature, and "$a_j$" are constants. | Emond et al. (1991) |
| $K_{O_2} = (9.12 \pm 3.53) * 10^{-6} * D^{1.47 \pm 0.08} * x^{-0.55 \pm 0.05}$ | Fonseca et al. (1996) |

FIG.6

Diameter and thickness of the micro-perforations used in this study.

| Film type | Diameter (μm) | Thickness (μm) |
|---|---|---|
| 1 hole | 96 | 50.7 ± 3.23 |
| 1 hole | 118 | 41.3 ± 2.84 |
| 1 hole | 160 | 40.0 ± 4.29 |
| 1 hole | 187 | 42.5 ± 2.28 |
| 2 holes | 115 | 43.3 ± 3.36 |
| 2 holes | 161 | 53.6 ± 5.25 |
| 2 holes | 200 | 61.8 ± 1.07 |
| 2 holes | 247 | 76.9 ± 1.61 |

FIG. 7

Comparison of the predicted OTR values with the experimental results. The values are given in cc day$^{-1}$

| Film Type | Youngquist (1970) | Fishman et. al. (1996) | Hirata et. al. (1996) | Fonseca et. al. (1996) | Experimental Static Method | Experimental Flow Through at 10 cc min$^{-1}$ (Adjusted) |
|---|---|---|---|---|---|---|
| 1 hole (96 μm) | 286.3 | 119.8 | 17.6 | 256.6 | 132.0 ± 3.0 | 184.8 ± 7.7 |
| 1 hole (118 μm) | 432.6 | 171.7 | 26.5 | 347.6 | 174.0 ± 6.4 | 190.3 ± 7.4 |
| 1 hole (160 μm) | 795.3 | 265.1 | 48.8 | 543.8 | 258.7 ± 0.2 | 304.9 ± 30.3 |
| 1 hole (187 μm) | 1086.4 | 319.8 | 66.7 | 683.9 | 375.2 ± 7.9 | 458.0 ± 20.7 |
| 2 holes (115 & 161 μm) | 1216.2 | 393.9 | 74.8 | 883.5 | 439.7 ± 8.8 | 487.5 ± 31.0 |
| 2 holes (200 & 247 μm) | 3089.8 | 670.0 | 189.6 | 1771.8 | 649.7 ± 24.7 | 815.0 ± 21.2 |

FIG. 20

RAPID METHOD TO EXPERIMENTALLY MEASURE THE GAS PERMEABILITY OF MICRO-PERFORATED FILMS

This application relates generally to methods to measure the gas permeability of films and more particularly to rapid methods to experimentally measure the gas permeability of micro-perforated films. This application also claims the benefit of pending U.S. Provisional Patent Application Ser. No. 60/096,067, filed Aug. 11, 1998.

BACKGROUND OF THE INVENTION

Fruits and vegetables continue maturation and senescence after harvest. At this stage, they are deprived of their normal source of water, mineral and other nutrients, which would normally be available to them from other parts of the plant, and are dependent upon their reserves for water and other minerals. The rate at which the produce loses water or other respirable minerals determines its shelf life. In other words, the higher the respiration and transpiration rates the lower will be the shelf life of the produce. Hence, if the respiration and transpiration of the produce can be decreased, the shelf life of the produce can be increased.

Controlled atmosphere packaging (CAP) and modified atmosphere packaging (MAP) are packaging systems that increase the shelf life of most produce by reducing the respiration of the produce. CAP is an intentional modification of the internal gaseous atmosphere of packaging and maintenance of that atmosphere at a specified condition throughout the cycle, regardless of the temperature or other environmental variations. The operating costs for CAP are very high, and it is suitable for fruits and vegetables that have a long shelf life. In MAP, only the initial internal conditions of the package are established. The atmosphere inside the package is altered due to respiration by the produce and permeation of gases and vapors through the plastic film. Thus, in designing MAP for produce, the plastic film is selected to match the respiration rate of the produce at the anticipated temperature of storage. The produce consumes oxygen during respiration and if this is not replaced by permeation through the packaging material, the atmosphere inside the package will become anaerobic, and the produce will respire anaerobically. When the fruit respires anaerobically, the glycolytic pathway replaces the Krebs cycle as the main source of energy needed by the plant tissues. Pyruvic acid is decarboxylated to form ethanol, which results in the development of off-flavors and tissue breakdown. Thus, high permeability to oxygen is essential for maintaining the minimum level of oxygen inside the package to prevent the produce from respiring anaerobically.

MAP of fruits and vegetables in plastic films is well suited for products like apples, peaches, tomatoes, etc., i.e. products that have low to medium respiration rates, but is not suitable for products like mushrooms, broccoli, leeks, etc., i.e. products that have very high rates of respiration. Even the most permeable films currently available for packaging have oxygen permeability of only 18,000–25,000 cc m$^{-2}$ day$^{-1}$ at 23–25° C., which are still insufficiently permeable, and result in over modification of the pack atmosphere.

In the past few years, many manufacturers have developed micro-perforated films. The diameter of the micro-perforations range from 40 to 200 microns. Gas transport through a micro-perforated film is the sum of the gas transport through the polymeric film and the micro-perforation. The gas transport through the plastic film is generally negligible, however, compared to the gas transport through the micro-perforations. These films offer very high transmission of oxygen due to the gas exchange through the micro-perforations. By altering the size and the thickness of the perforations, different permeabilities can be obtained. Micro-perforated films show a tremendous potential for extending the shelf life of high-respiring produce. Many researchers have used these films with success to extend the shelf life of various products. They have also developed mathematical models to predict gas exchange through the micro-perforations, but to date experimental methods to determine permeation rates have not been developed.

The American Society for Testing Materials (ASTM) provides three methods for measuring the oxygen transmission through barrier plastic films (i.e. films without perforations). The methods are: (i) manometric method (ASTM D 1434), (ii) volume method (ASTM D1434) and (iii) coulometric sensor method (ASTM D3985). The first two methods use absolute pressure differences. When measuring the permeability of films with micro-perforations, care should be taken that there is no absolute pressure difference across the film because in the presence of absolute pressure difference there will be viscous flow along with diffusive flow. So, the pressure method and volume method, which uses absolute pressure difference, cannot be used in the case of micro-perforated films. The coulometric sensor method, which does not have absolute pressure difference, has a potential for being used for micro-perforated films. In the case of perforated films, the pressure drop across the film in this method has to be minimized to zero to prevent viscous flow and short circuiting of the carrier gas through the perforations. Present methods are not adopting this technique to minimize the pressure drop. Another drawback with this method is that currently available systems utilizing this method have a maximum range of 155, 000 cc m$^{-2}$ day$^{-1}$, but the range of permeabilities of micro-perforated films exceeds that range. Also, the use of this system for measurement of permeability of micro-perforated films does not appear in the literature. So, there is a present need for a setup for measuring the permeability of micro-perforated films.

SUMMARY OF THE INVENTION

Micro-perforated films are increasingly used in modified atmosphere packaging (MAP) of fruits and vegetables with high respiration rates. In the design of MAP for fruits and vegetables, the knowledge of film permeability is essential. The goal of the present invention is to provide a novel setup to measure the permeability of micro-perforated films to oxygen, and to use the results obtained to evaluate the different mathematical models available for predicting the gas transport through micro-perforated films.

Static and flow through methods were used to study the oxygen transmission rate (OTR) through perforations. The static method simulated the real package situation, but was very time consuming. On the other hand, the flow through method was relatively simple and took less time to give results. It however gave higher values than those obtained by the static method. The OTR data obtained from the static setup was correlated with the OTR data of flow-through by a regression equation.

Published models for predicting gas exchange through micro-perforations were evaluated using experimental data obtained using the static method for six different films. The model proposed by Fishman et al. (1996)(where effective length of diffusion=thickness of the film+radius of the perforation) had a very good agreement with the results obtained through experimentation. The model presented by Fishman et al. was mathematically shown to explain the diffusion phenomena through micro-perforations.

One preferred embodiment of the present invention is a rapid flow-based method to measure experimentally the oxygen permeability of micro-perforated films, comprising providing a diffusion cell having first and second compartments separated by a test film having micro-perforations, each compartment having an inlet and an outlet for gas flushing, sweeping the test film with a measured flow of pure nitrogen gas in the first compartment and with a measured flow of oxygen in the second compartment, while maintaining precise localized equal pressures on both side of the micro-perforations, determining the volume fraction concentration of oxygen at the outlet of the first compartment; and computing the oxygen transmission rate (OTR) across the test film in cc days$^{-1}$ utilizing the formula $$OTR_{flow} = 1440 fx$$

where f is the oxygen flow rate in cc min$^{-1}$ and x is the volume fraction oxygen concentration at the outlet of the first compartment.

Another preferred embodiment of the present invention is a static-based method to measure experimentally the oxygen permeability of micro-perforated films, comprising providing a diffusion cell having a nitrogen gas receiving compartment of volume V separated from the atmosphere by a test film, the compartment having an inlet and an outlet for gas flushing, purging the oxygen from the nitrogen gas receiving compartment with nitrogen gas, measuring the volume fraction concentration of oxygen ($c_o$) within the nitrogen receiving compartment at time 0 to account for possible oxygen leakage through the micro-perforations, determining the volume fraction concentration of oxygen (c) within the purged nitrogen gas receiving compartment after the passage of time t, and computing the oxygen transmission rate (OTR) across the test film in cc day$^{-1}$ from the slope of the line generated by the equation $$\ln\left(\frac{\Delta c}{\Delta c_o}\right) = -\frac{OTR}{V} t \qquad (2)$$

where $c_o$ is the initial oxygen concentration within the nitrogen gas receiving compartment.

It is a principal object of the present invention to provide a rapid method to experimentally measure the permeability of micro-perforated films.

It is a further object of the present invention to evaluate based on the experimental data the different mathematical models available for predicting the gas transport through micro-perforations.

BRIEF DESCRIPTIONS OF THE DRAWING FIGURES

Figures:

FIG. 1. Schematic of the test cell for the flow through system.

Figure 2:
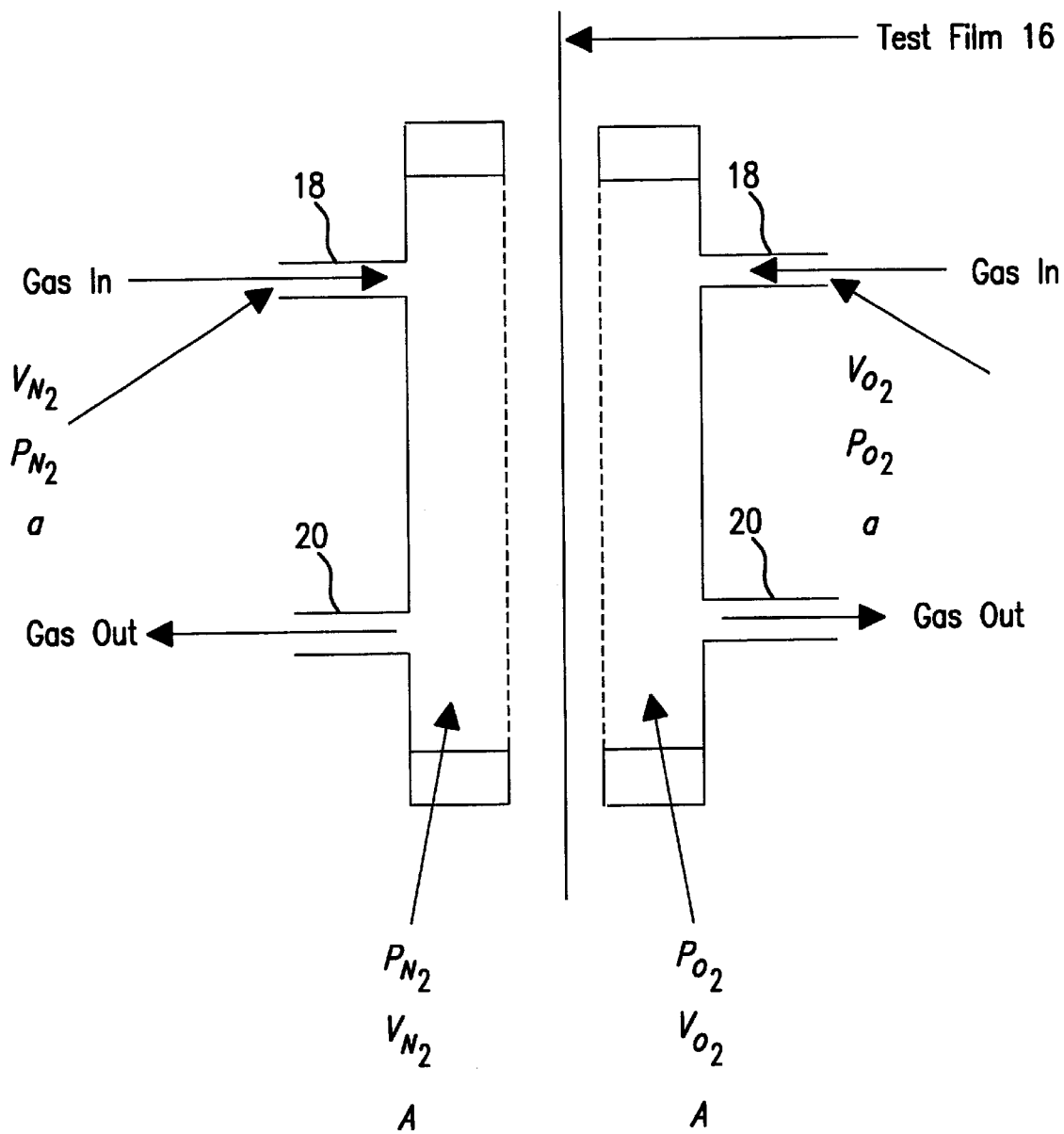

FIG. 2. Schematic of the test cell of FIG. 1 illustrating the different parameters.

Figure 3A:
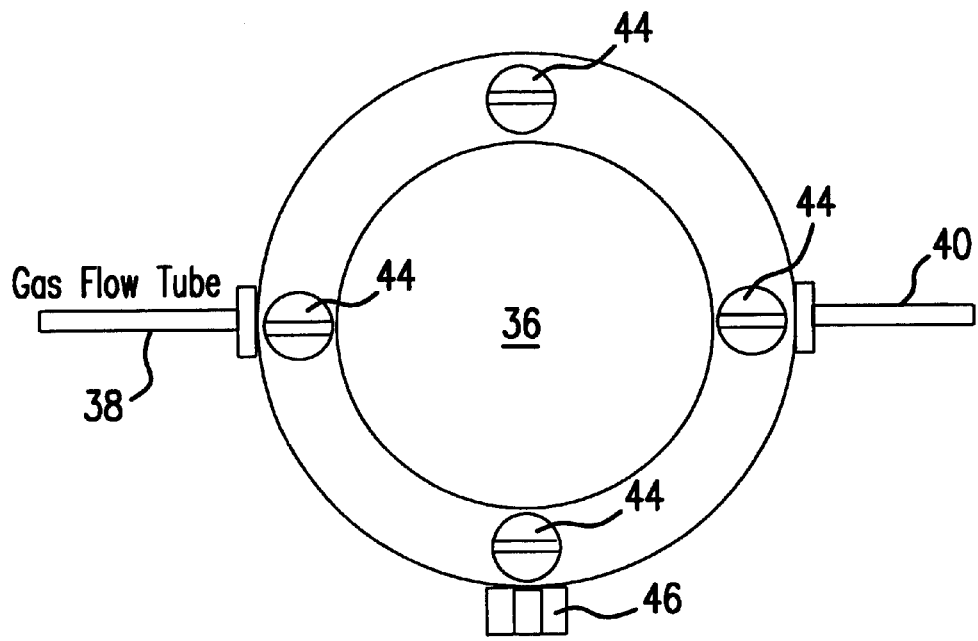
Figure 3:
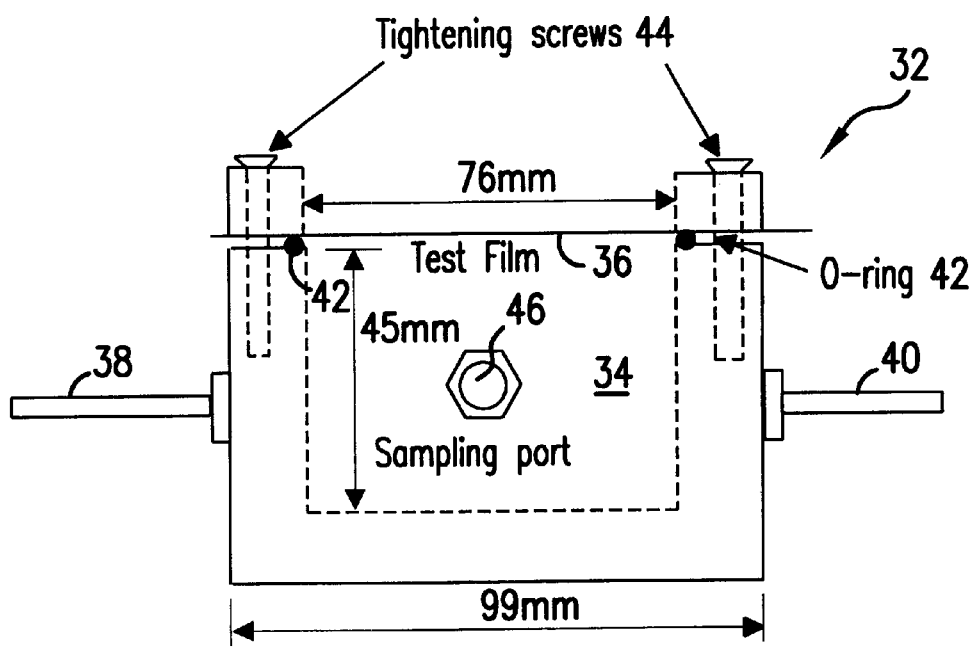

FIG. 3. Schematic of the test cell for static system.

FIG. 3a. A top view of the test cell of FIG. 3.

Figure 4:
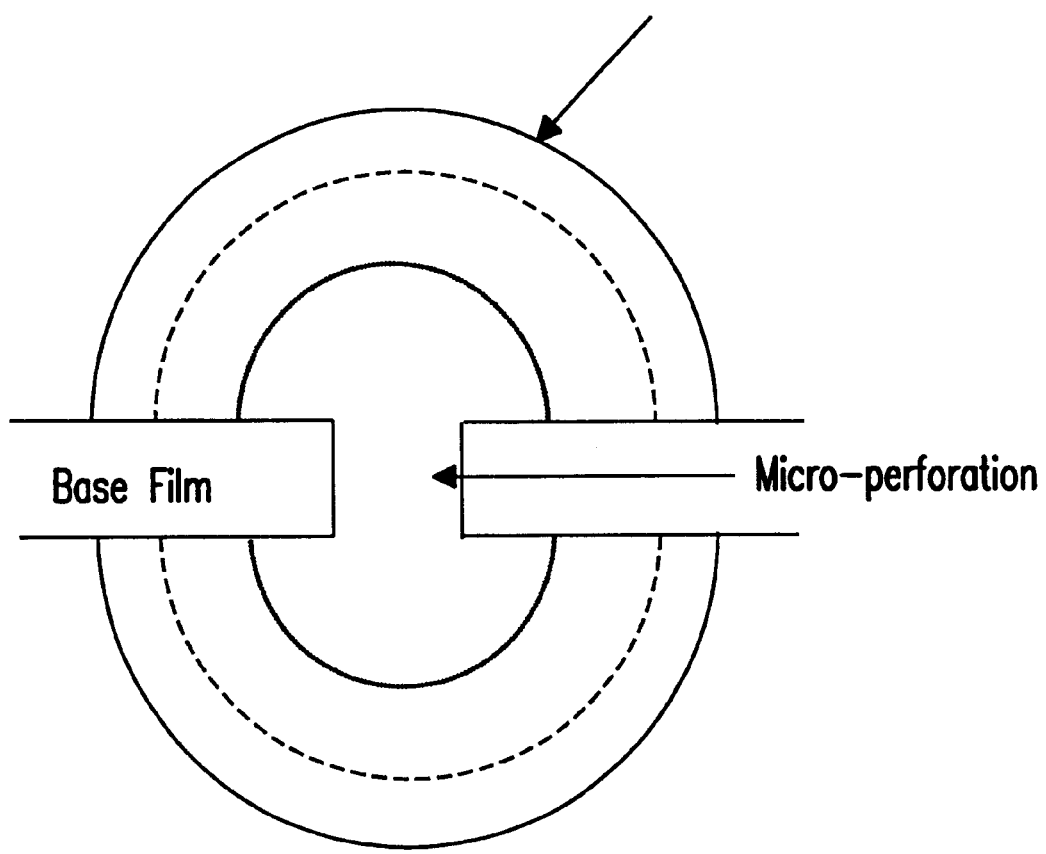

FIG. 4. Concentration distribution across the micro-perforations.

Figure 5:
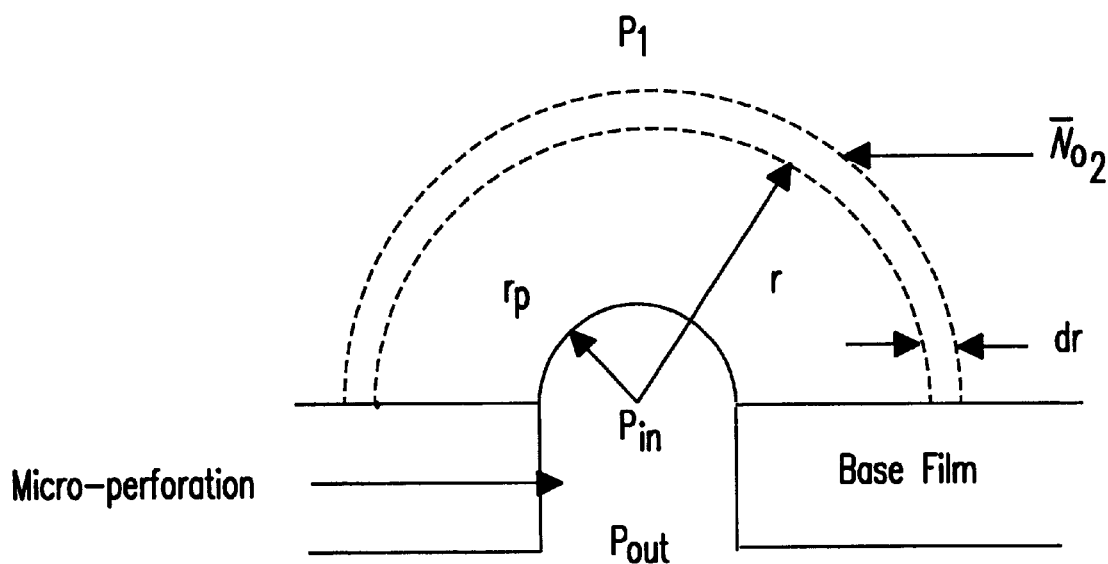

FIG. 5. Location of different variables for studying flux through micro-perforations.

FIG. 6. Models for predicting gas exchange through perforations.

FIG. 7. Diameter and thickness of the micro-perforations used in the experiments.

Figure 8:
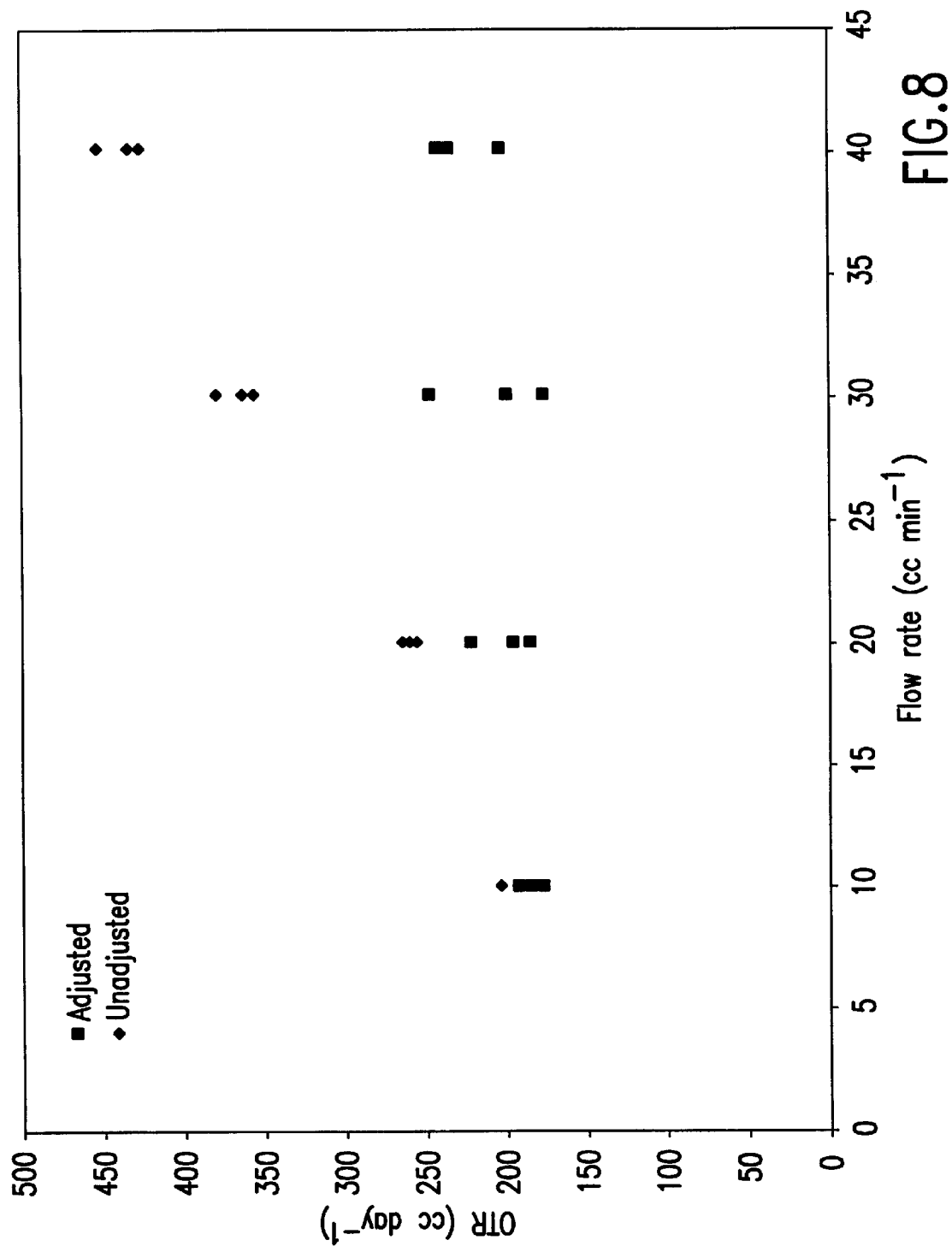

FIG. 8. OTR as a function of flow rate for the films with one hole (dia. 96 $\mu$m).

Figure 9:
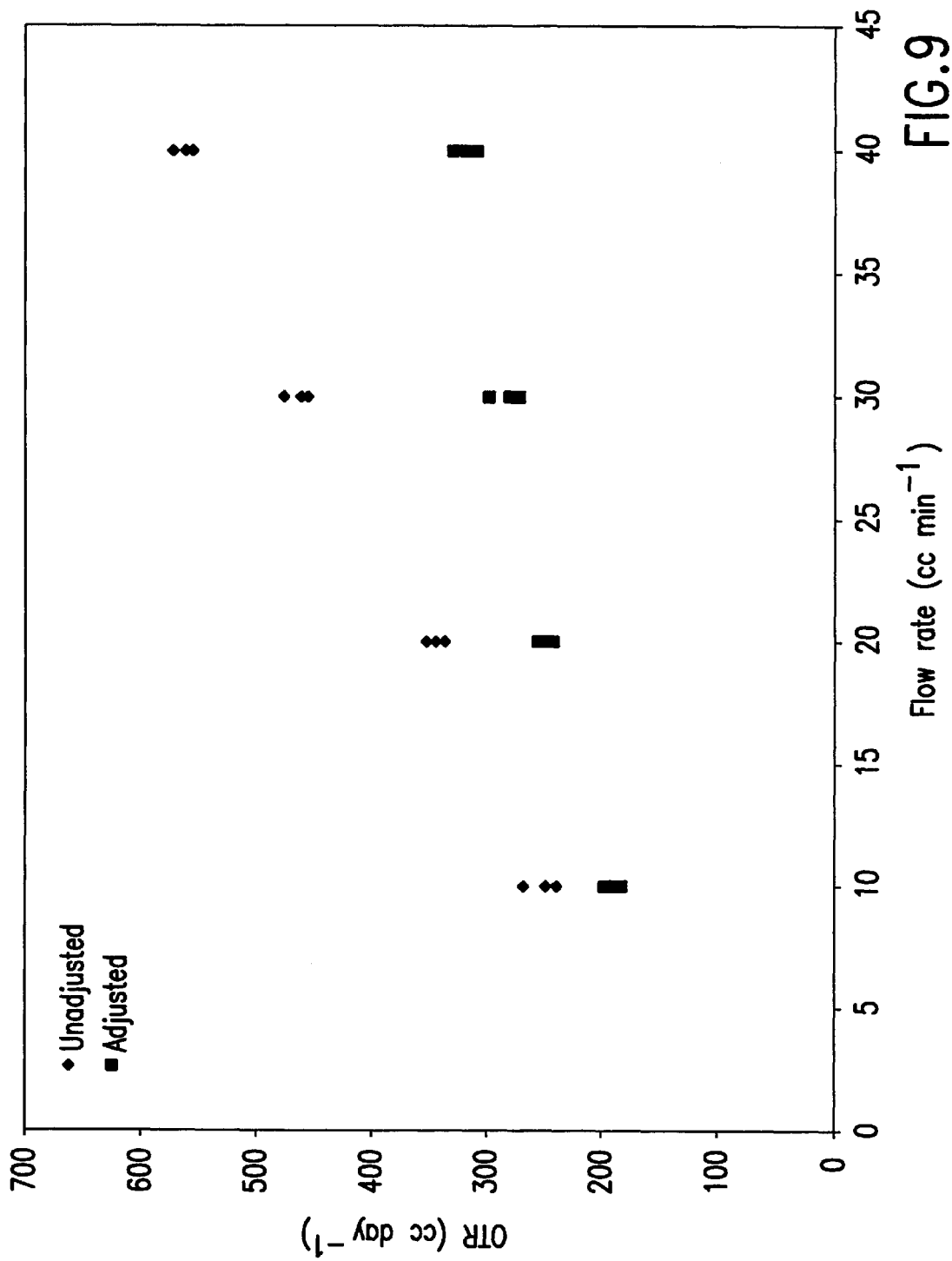

FIG. 9. OTR as a function of flow rate for the films with one hole (dia. 118 $\mu$m).

Figure 10:
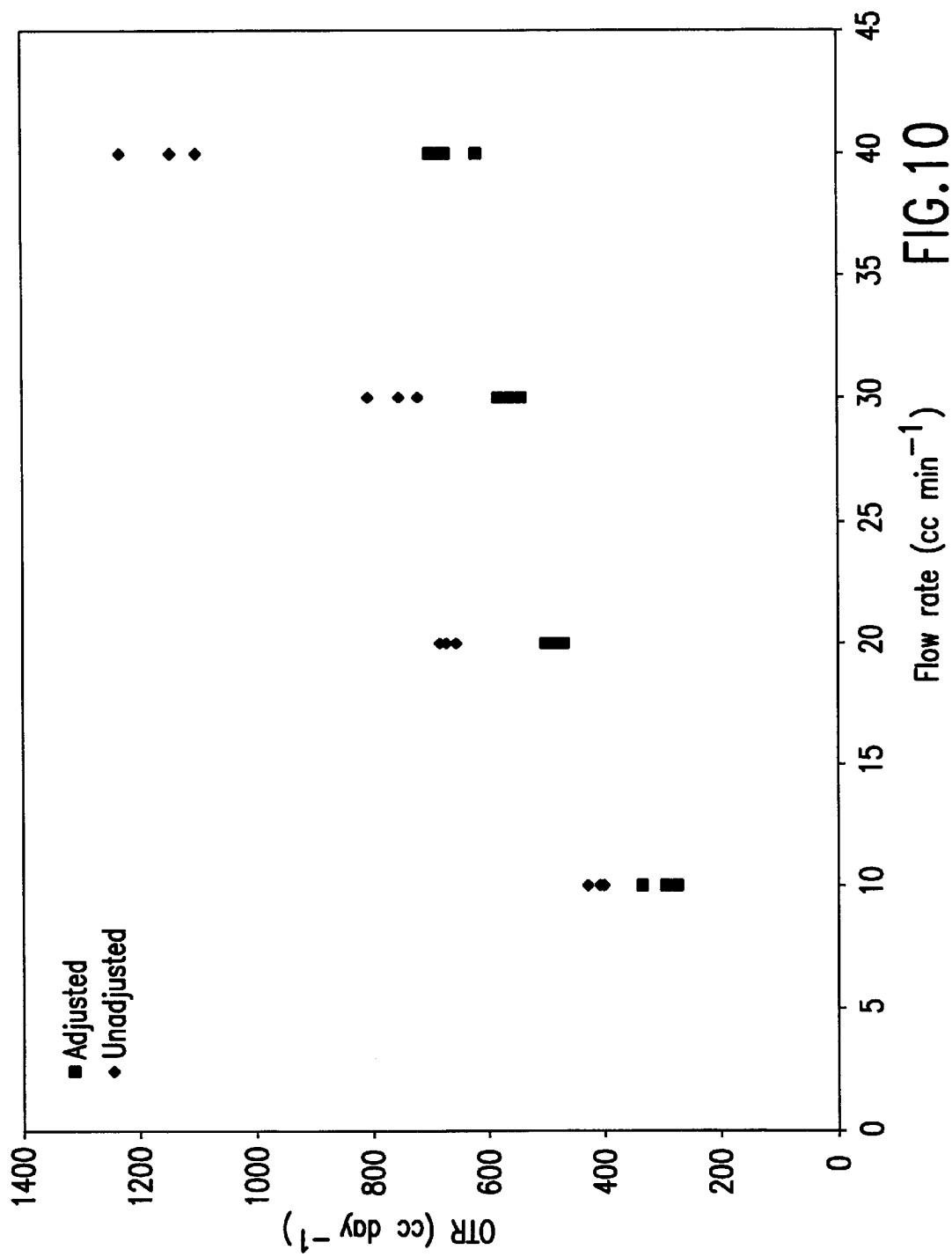

FIG. 10. OTR as a function of flow rate for the films with one hole (dia. 160 $\mu$m).

Figure 11:
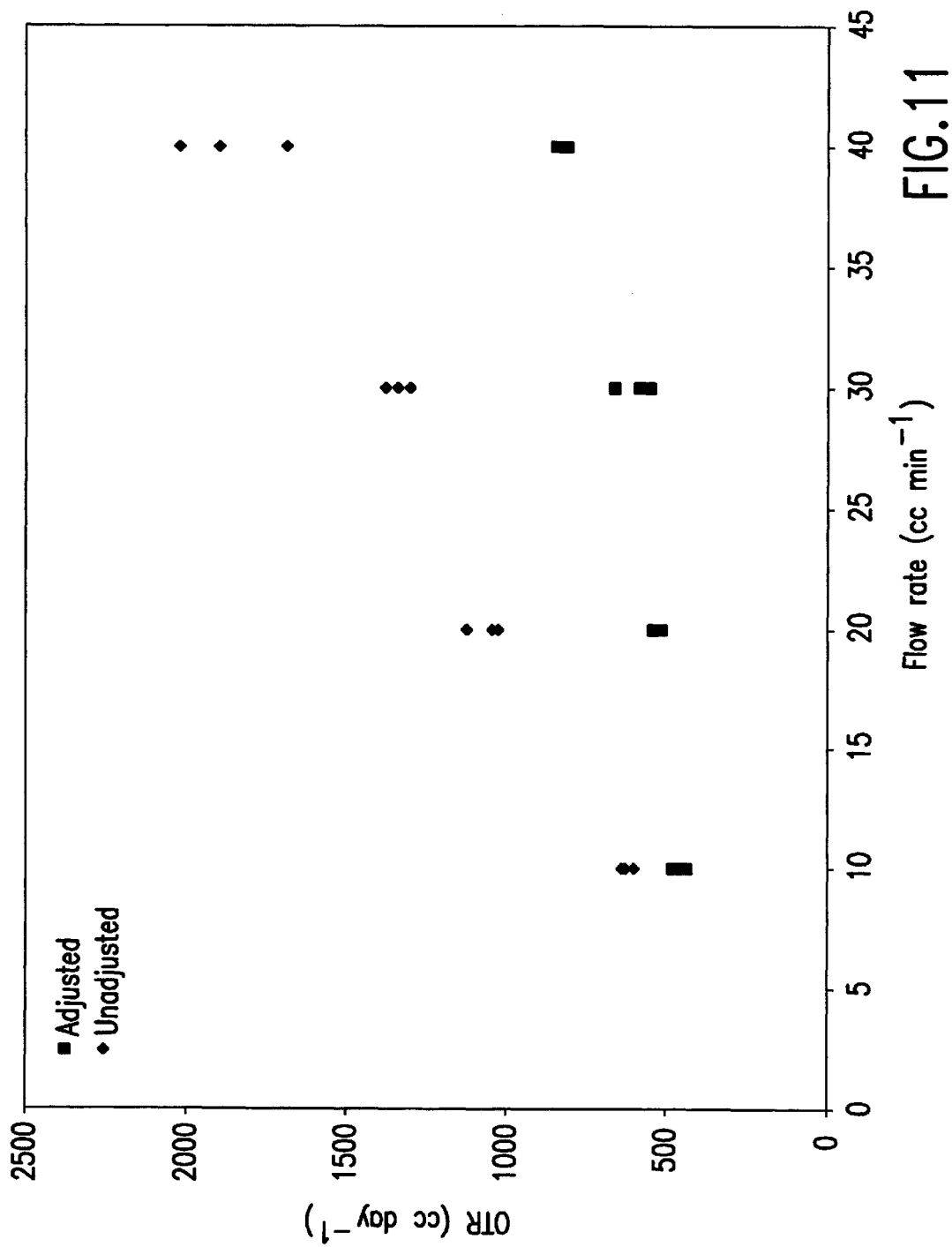

FIG. 11. OTR as a function of flow rate for the films with one hole (dia. 187 $\mu$m).

Figure 12:
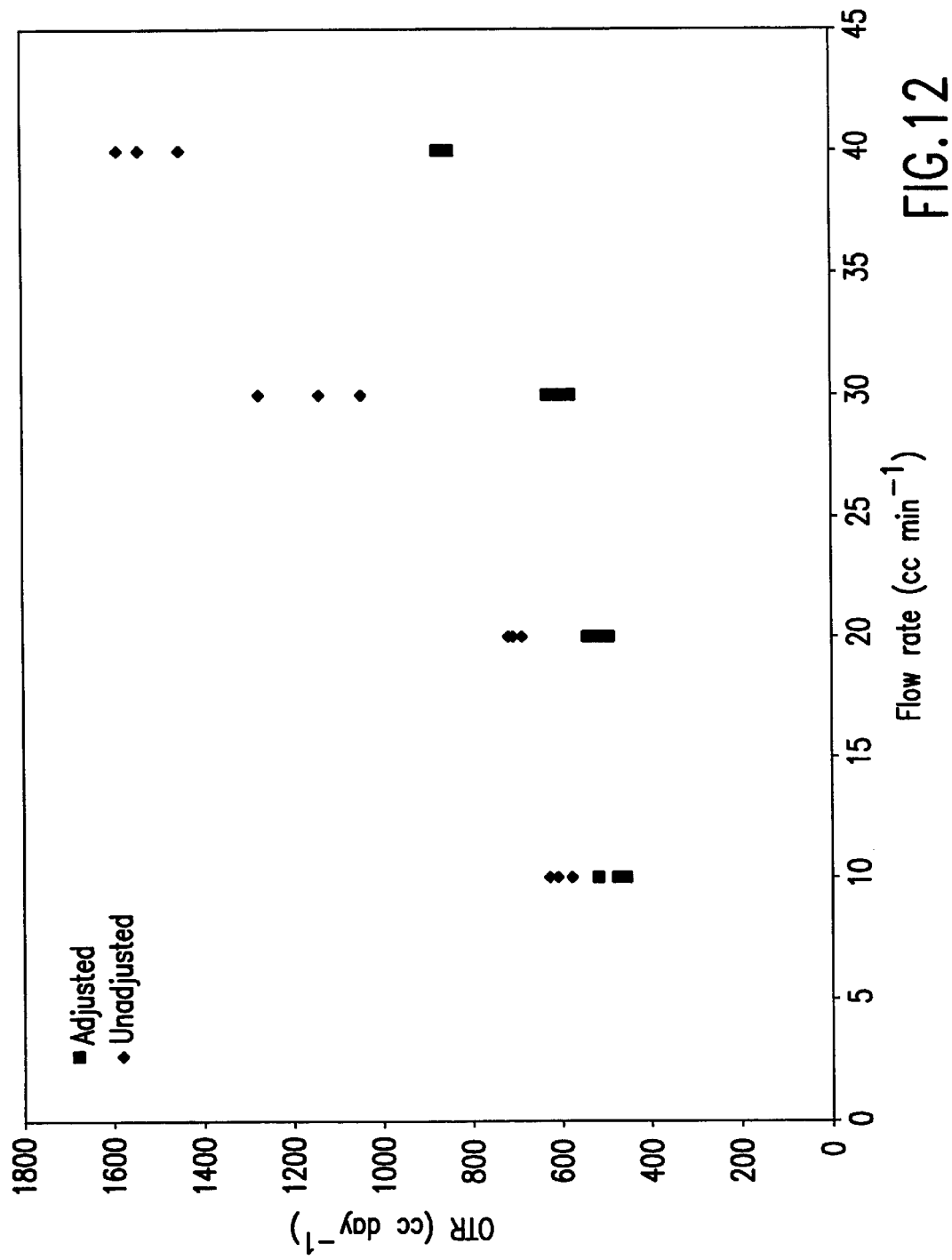

FIG. 12. OTR as a function of flow rate for the film with two holes (dia. 161 and 115 $\mu$m).

Figure 13:
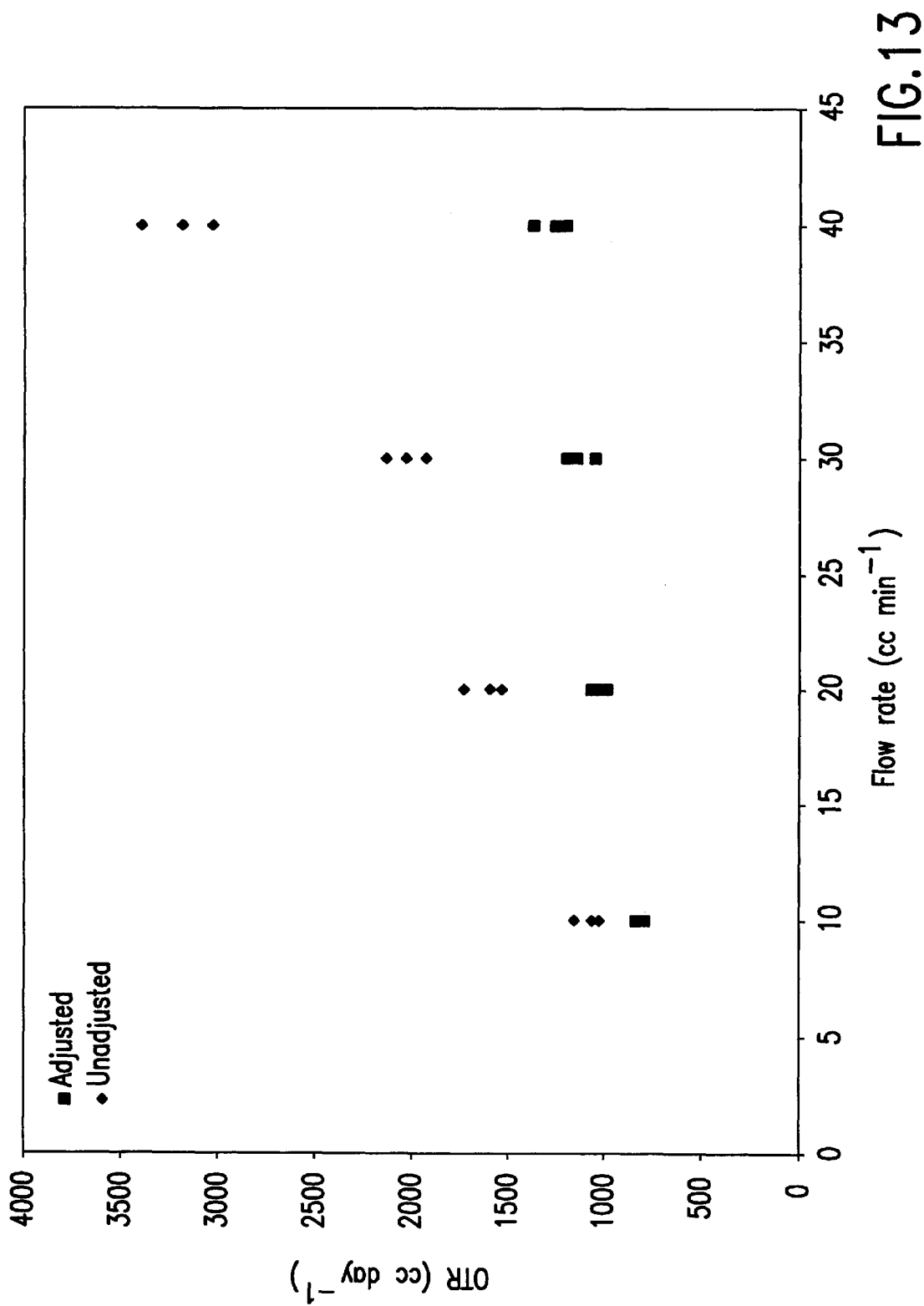

FIG. 13. OTR as a function of flow rate for the film with two holes (dia. 247 and 200 $\mu$m).

Figure 14:
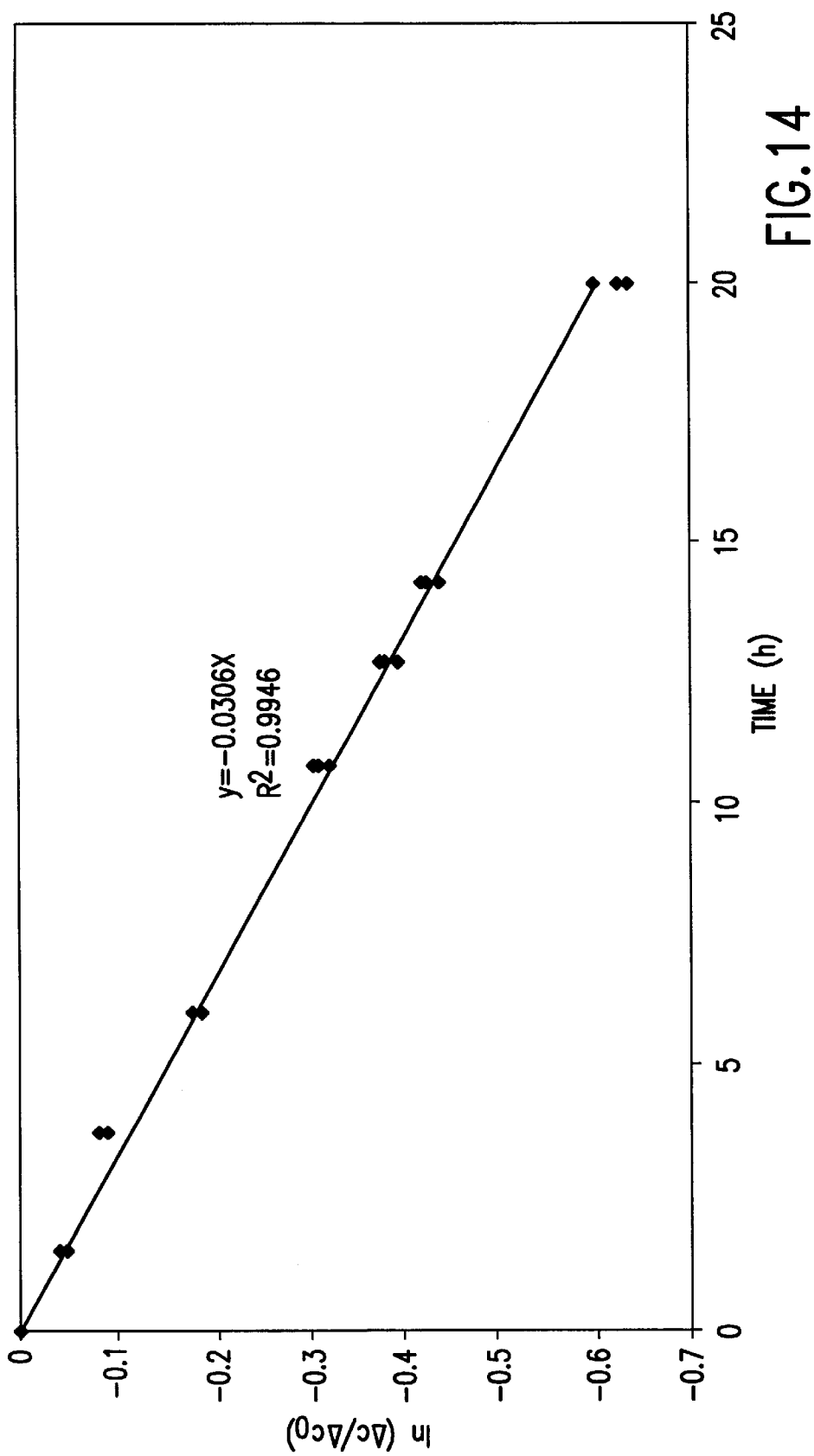

FIG. 14. Plot of $\ln(\Delta c/\Delta c_o)$ vs. time for the film with hole diameter of 96 $\mu$m.

Figure 15:
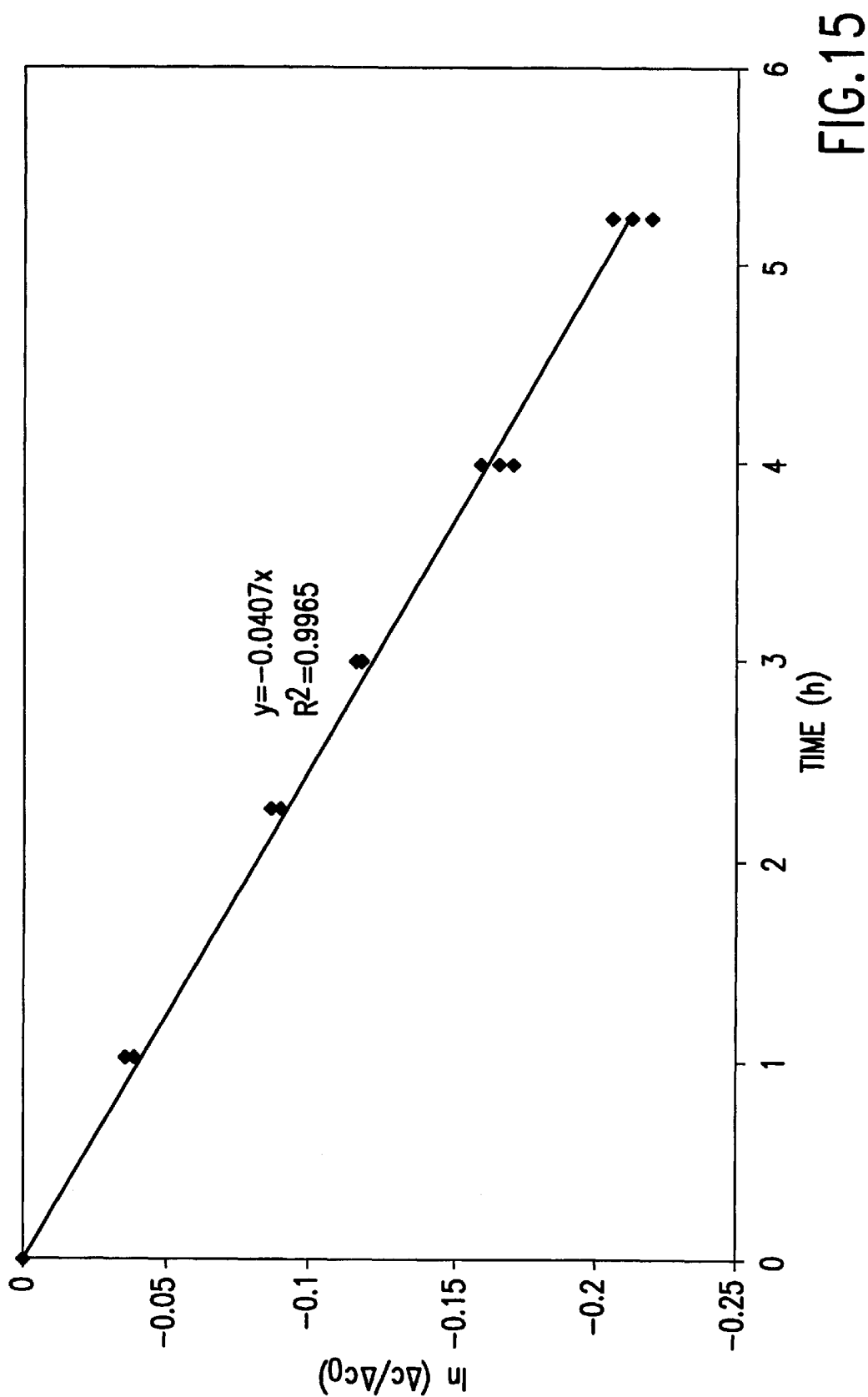

FIG. 15. Plot of $\ln(\Delta c:\Delta c_o)$ vs. time for the film with hole diameter of 118 $\mu$m.

Figure 16:
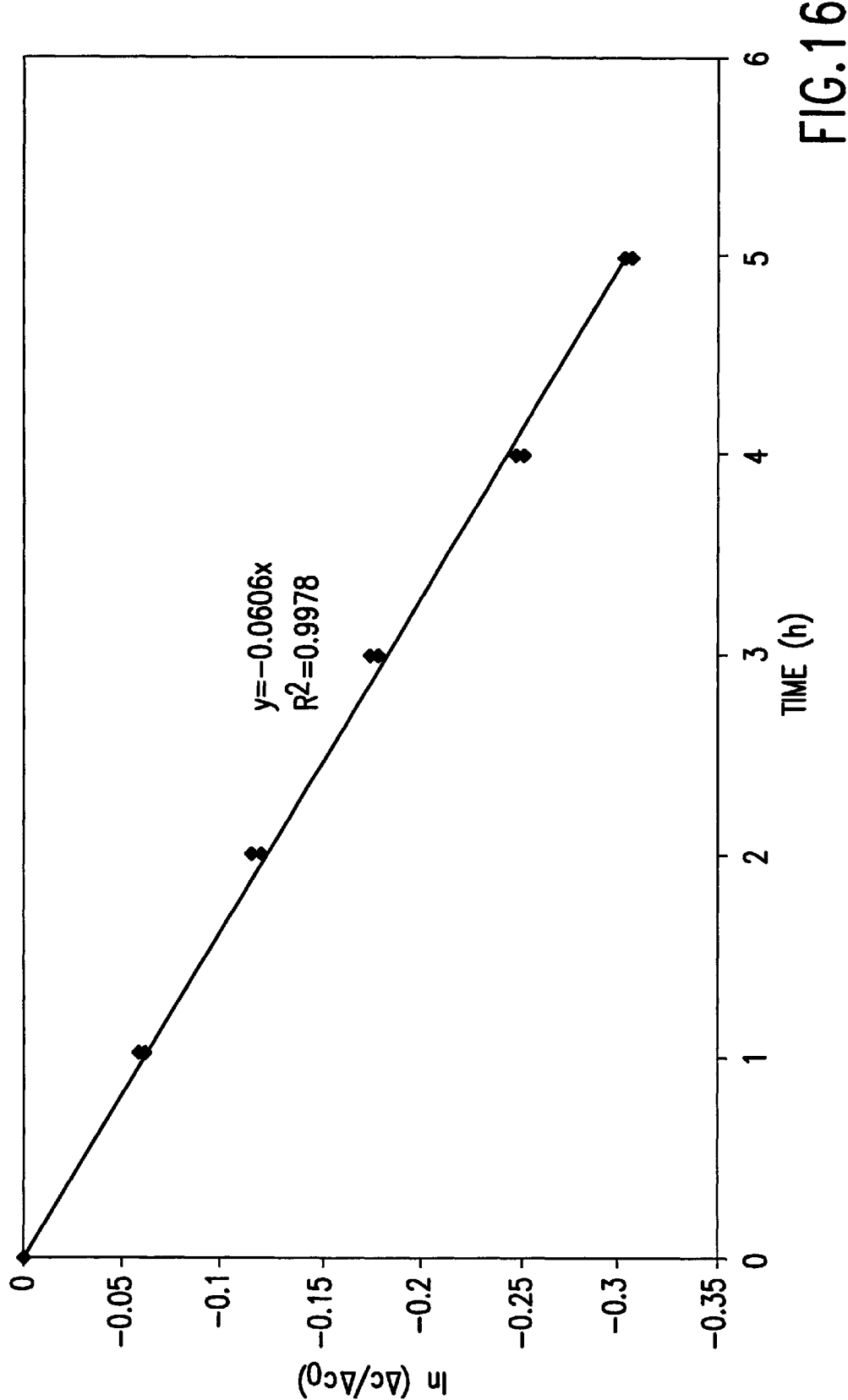

FIG. 16. Plot of $\ln(\Delta c/\Delta c_o)$ vs. time for the film with hole diameter of 160 $\mu$m.

Figure 17:
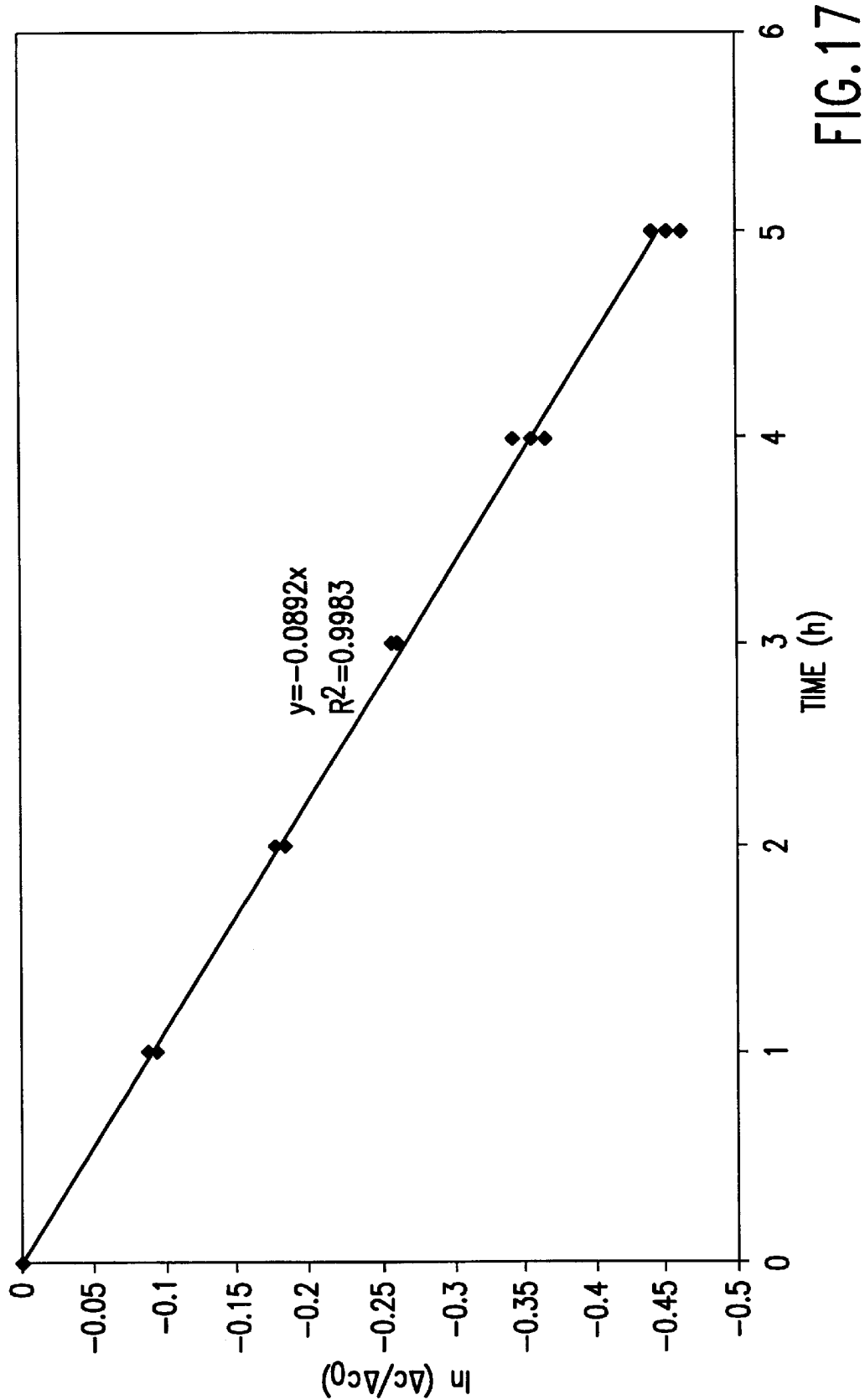

FIG. 17. Plot of $\ln(\Delta c/\Delta c_o)$ vs. time for the film with hole diameter of 187 $\mu$m.

Figure 18:
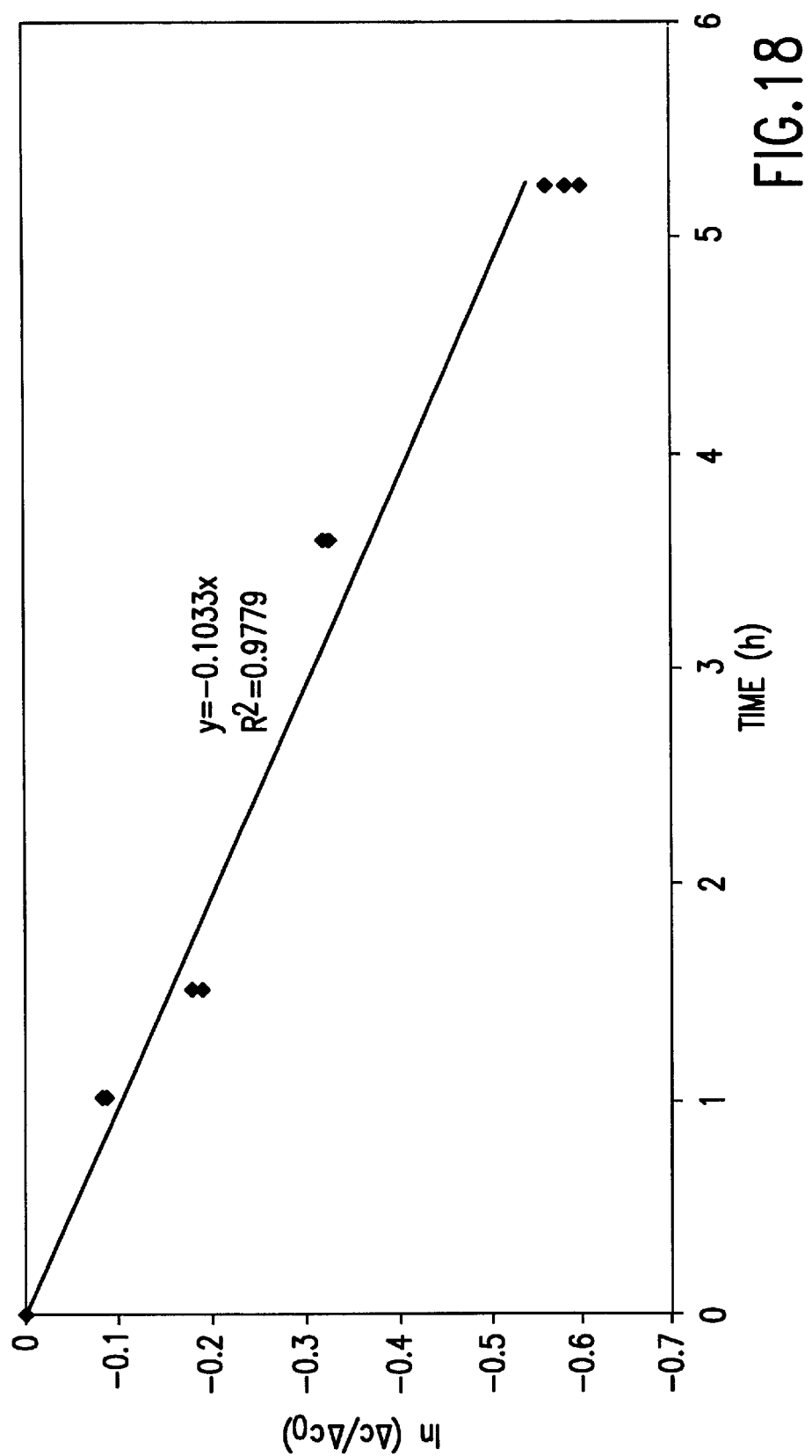

FIG. 18. Plot of $\ln(\Delta c/\Delta c_o)$ vs. time for the film with two holes with dia meter s of 161 and 115 $\mu$m.

Figure 19:
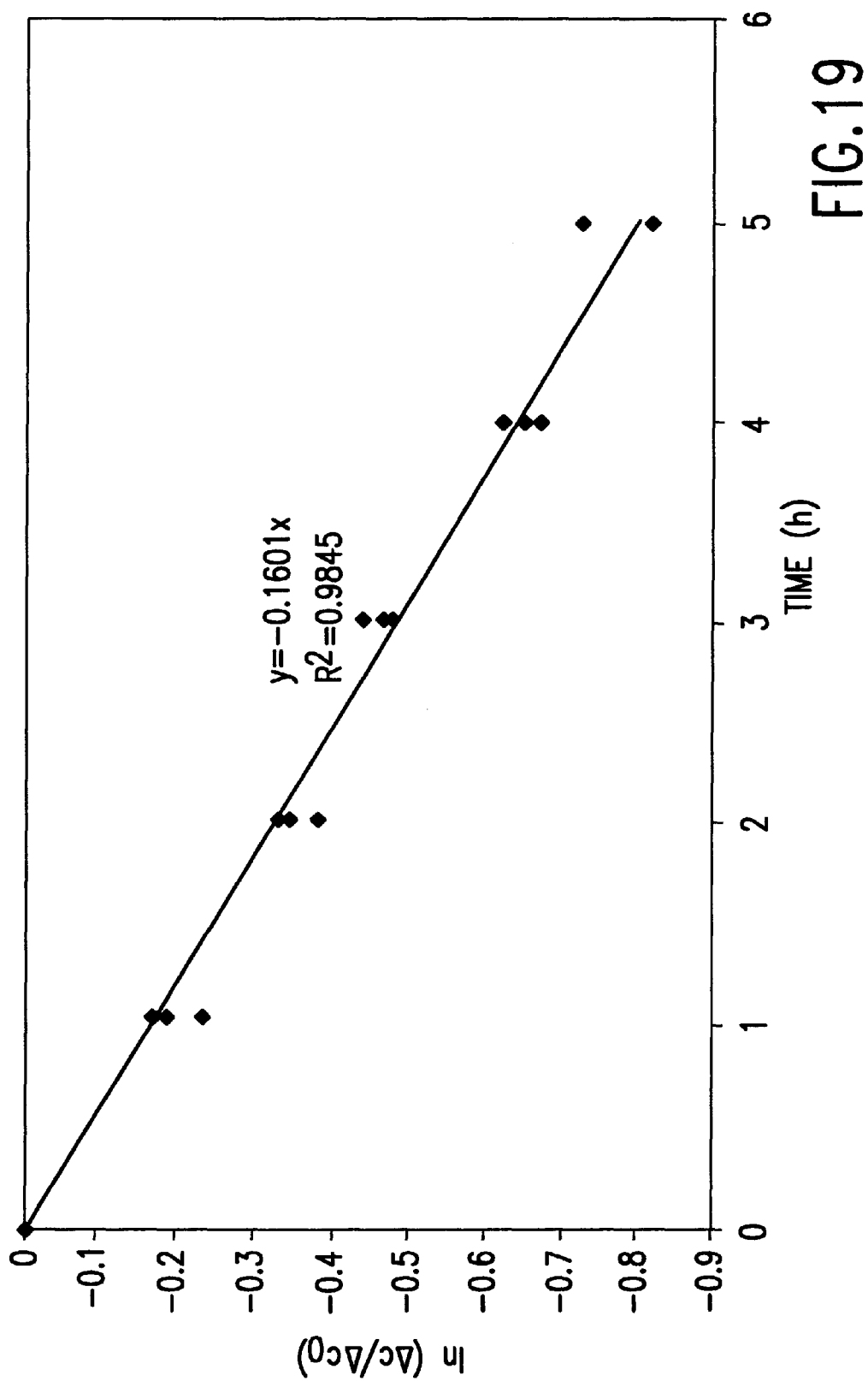

FIG. 19. Plot of $\ln(\Delta c/\Delta c_o)$ vs. time for the film with two holes with diameters of 247 and 200 $\mu$m.

FIG. 20. Comparison of predicted OTR values with experimental results in cc day$^{-1}$.

DETAILED DESCRIPTION OF THE PREFERRED EMBODIMENTS

Micro-perforated films were obtained from EPL Technologies, Inc., 2 International Plaza, Suite 245, Philadelphia, Pa. 19113-1507. The perforations were made in the base film (in this case polypropylene) by using mechanical spark. The company designated the perforation sizes as small or large. A total of six films were tested. Two films of each designation (small and large) with one perforation and one film of each designation with two perforations were used to study the oxygen transmission rate through micro-perforations.

Determination of Diameter and Thickness of Micro-perforations

For determining their diameters, the micro-perforations were observed under a microscope (Zeiss Photoscope II), which was connected to a monitor and a printer (Sony, Japan). Photographs of the magnified micro-perforations were obtained using the printer. A photograph of a 0.1 mm stage micrometer was used for calibration. The diameter of the micro-perforation was measured at four places. Since some of the micro-perforations had an elliptical shape the geometric average of the readings was designated as the characteristic diameter (equation 1) in order to minimize the error in the calculation of the area of the micro-perforation.

$$d_{av} = \sqrt[4]{d_1 d_2 d_3 d_4} \qquad (1)$$

where $d_{av}$ is the average diameter of the hole, $d_1$, $d_2$ $d_3$ and $d_4$ are the diameters at four different locations of the micro-perforation.

For determining the thickness, micro-perforated plastic films were sliced through the micro-perforation with a razor blade. The films were placed with the cut edge up, onto scanning electron microscopy (SEM) stubs with double sticky tabs. Colloidal silver was placed at the adhesive edge to ensure electrical conductivity and the films were sputter coated with 10 nm of gold/palladium in BAL-TEC SCD050 (Boston, Mass.) sputter-coater. SEM images were generated at 10 kV on a JOEL 5400 SEM (Peabody, Mass.) and recorded on Polapan 100 film and transferred to Princeton-Gamma Tech's Integrated Microanalyzer for Imaging and X-ray (IMIX v.8, Princeton, N.J.) to generate measurements of the perforation's thickness. Cut edges of the micro-perforations were digitized to generate measurements in microns. The SEM was performed at the Electron Microscope Facility for Life Sciences in the Biotechnology Institute at The Pennsylvania State University.

Flow Through System

A schematic of the setup used to obtain data is shown in FIG. 1. The setup consists of a diffusion cell 10. It is divided into two compartments 12,14 by the test film 16, each having an inlet 18 and outlet tube 20 for gas flushing. One part of the cell had a 3" O-ring 22 to ensure proper sealing of the film 16 and prevent any leakage. Thus, the sample area of the test as shown in FIG. 1 was 46 cm². For measuring the OTR a sample of the film was cut out. The O-ring 22 and the sealing rim 24 were lightly greased with silicone grease. The film 16 was then placed in the cell 10 and flattened to remove wrinkles or creases. The cell 10 was then closed by tightening screws 26 placed at each corner of the cell 10. On one side of the film 16 pure nitrogen was allowed to sweep the film 16 and on the other side oxygen swept the film 16. The flow rates of both $O_2$ and $N_2$ were controlled by using a float type flowmeter 28 (Model #FL 220, Omega Engineering, Inc., Stamford, Conn.). The graduations in the float type flowmeter 28 could not differentiate small changes in the flow rate (difference of less 1 cc min$^{-1}$), so the flow rate of the gas was also checked using a 50 cc soap bubble flowmeter 30 (not shown)(Supelco, Bellefonte, Pa.) to get a more accurate reading of the flowrate.

Theoretical Analysis

By using Bernoulli's principle (MaCabe et al. 1993), we get the pressure on each side of the cell (see FIG. 2):

$$P_{N2} = \frac{\rho_{N_2}}{2}[v_{N_2}^2 - V_{N_2}^2] + p_{N_2}$$

$$P_{O2} = \frac{\rho_{O_2}}{2}[v_{O_2}^2 - V_{O_2}^2] + p_{O_2}$$

where

P is the gage pressure in the cell; p is the gage pressure in the tubing; ρ is the density of the gas; v is the flow velocity of the gas in the tubing; and V is the flow velocity in the cell. For the pressure inside the cell to be equal:

$$\frac{\rho_{N_2}}{2}[v_{N_2}^2 - V_{N_2}^2] + p_{N_2} = \frac{\rho_{O_2}}{2}[v_{O_2}^2 - V_{O_2}^2] + p_{O_2}$$

or, $$\frac{\rho_{N_1} v_{N_1}^2}{2}\left[1 - \left(\frac{a}{A}\right)^2\right] + p_{N_2} = \frac{\rho_{O_2} v_{O_2}^2}{2}\left[1 - \left(\frac{a}{A}\right)^2\right] + p_{O_2}$$

Where a is the area of the tubing and A is the area of the test cell. Assuming the pressure inside the tubings is the same, one gets:

$$\frac{v_{N_2}}{v_{O_2}} = \sqrt{\frac{\rho_{O_2}}{\rho_{N_2}}} = \sqrt{\frac{M_{O_2}}{M_{N_2}}}$$

Where M is the molecular weight of the gas. Hence, for the pressure to be equal on both sides the ratio of flow rates should be equal to the reciprocal of the square root of their molecular weights.

Gas Analysis

Five ml of gas was taken from the sampling port using a hypodermic syringe (Hamilton Co., Reno, Nev.). The sample was analyzed using a gas chromatograph (W5980 Series II, Avondale, Pa.) containing a 6'×⅛" molecular sieve column (Alltech, Deerfield, Ill.) and a thermal conductivity detector. The concentration was determined by comparing the area of the peak with that of standard gases. The oxygen transmission rate was determined by the equation:

$$OTR = 1440 fx$$

where

OTR=oxygen transmission rate, cc day$^{-1}$ f=flow rate, cc min$^{-1}$ x=oxygen concentration at the outlet of the nitrogen side, volume fraction.

Static System

A schematic of the static cell is shown in FIG. 3. The static cell consists of a diffusion cell 32 having a nitrogen gas-receiving compartment 34 of volume V separated from the atmosphere by a test film 36. The nitrogen gas-receiving compartment has an inlet 38 and an outlet 40 for gas flushing. The static cell is set up in a manner similar to the flow through cell of FIG. 1, using an O-ring 42 and tightening screws 44.

The OTR of the base film was experimentally determined using Ox-Tran (Modem Controls, Inc., Minneapolis, Minn.). The average OTR for the base film at 23° C. was found to be 15 cc m$^{-2}$ day$^{-1}$. Thus, the oxygen transfer through the film 36 is negligible compared to the oxygen transfer through the micro-perforation. Using this assumption, the OTR through a micro-perforation is given by the following equation:

$$\frac{dc}{dt} = \frac{OTR(c_{air} - c)}{V}$$

where V is the volume of the cell 32. Integrating, the above equation, from $c_{air}$ to $c_o$ one gets:

$$c_{air} - c = (c_{air} - c_o)e^{-\frac{OTR}{V}t}$$

where $c_o$ is the initial oxygen concentration inside the cell 32. Putting, $\Delta c_o = c_{air} - c$, and $\Delta c = c_{air} - c$, and taking the natural logarithm of both sides of above equation one gets:

$$\ln\left(\frac{\Delta c}{\Delta c_o}\right) = -\frac{OTR}{V}t \quad (2)$$

The slope of the line given by equation (2) can determine the OTR.

For measuring the rate of diffusion, nitrogen was allowed to flow through the cell 32 for 30 minutes at a flow rate of 50 cc min$^{-1}$, so that the cell 32 is completely purged with nitrogen and there is no detectable amount of oxygen in the cell 32. Then valves were closed and a sample was taken out of a sampling port 46 after a desired time interval and analyzed using gas chromatography (GC).

When a sample is taken out from the static cell 32, a small vacuum is created near the micro-perforation, due to which a certain amount of air comes into the cell and into the syringe. Thus, the reading is actually the amount of oxygen diffused plus the air that entered the syringe because of drawing the sample. To account for the air entered because of drawing the sample, two measures were taken. First, a concentration reading was taken at time zero and secondly, the cell was purged for each reading. Thus, if a concentration was to be measured after a time interval of three hours, the cell was first purged with nitrogen and left closed for three hours for taking the measurement. The same procedure was used for all other cases. The concentration at any time was taken as the concentration obtained at that time minus the concentration at time zero. The measurements were done at room temperature (23±2° C.).

Mathematical Analysis of Diffusion Through Micro-Perforation

For diffusion through small pores, it is difficult to measure the concentration just at the end of the pore. The concentration is generally measured some distance away from the pore. Hence, when modeling diffusion through a micro-perforation, three cases need to be considered. First is the diffusion of the gas into the micro-perforation, the diffusion through the micro-perforation and then the diffusion out of the micro-perforation.

For determining the flux through the micro-perforation out to the atmosphere, two assumptions are made. The assumptions are given below.

1. The concentration at a radial distance r from the center of the outer section of the micro-perforation is constant (see FIG. 4).
2. The concentration at a distance $r_p$ (=radius of the micro-perforation), is the same as that at the top section of the micro-perforation.

This is considered a case for A diffusing through stagnant non-diffusing B. For calculating the diffusion, a hemispherical element is taken at distance r from the center of the perforation (FIG. 5). Since this is a case of diffusion through varying cross-section we define the flux $N_{o2}$, as:

$$N_{O_2} = \frac{\overline{N}_{O_2}}{A} \quad (3)$$

where $\overline{N}_{O2}$ is kg mol of oxygen diffusing per second and A is the cross-sectional area. At steady state $\overline{N}_{O2}$ will be constant. The cross-sectional area at a distance r is $2\pi r^2$. Thus, equation (3) can be written as:

$$N_{O_2} = \frac{\overline{N}_{O_2}}{2\pi r^2}$$

The flux $\overline{N}_{O2}$, is given in the differential form by the equation:

$$N_{O_2} = \frac{\overline{N}_{O_2}}{2\pi r^2} = -\frac{D_{O_2-N_2}P}{RT} \frac{dp}{(1-p/P)dr}$$

Rearranging and integrating equation (3.13) between $r_p$ and some $r_1$ a large distance away, $$\frac{N_{O_2}}{2\pi} \int_{r_p}^{r_1} \frac{dr}{r^2} = -\frac{D_{O_2-N_2}P}{RT} \int_{P_{in}}^{p_1} \frac{dp}{1-p/P} \quad (3)$$

or, $$\frac{\overline{N}_{O_2}}{2\pi}\left(\frac{1}{r_p} - \frac{1}{r_1}\right) = \frac{D_{O_2-N_2}P}{RT} \ln\left(\frac{P-p_1}{P-p_{in}}\right)$$

Since $r_1 \gg r_p$, $l/r_1 \cong 0$. Hence, the total amount of oxygen diffusing out through the hole per second is given as:

$$\overline{N}_{O_2} = 2\pi r_p \frac{D_{O_2-N_2}P}{RT} \ln\left(\frac{P-p_1}{P-p_{in}}\right)$$

The flux through the top of the micro-perforation can be obtained by dividing equation (3) by $\pi r_p^2$:

$$N_{O_2} = \frac{D_{O_2-N_2}P}{RT(r_p/2)} \ln\left(\frac{P-p_1}{P-p_{in}}\right) \quad (4)$$

Similarly, the equation for diffusion of oxygen into the micro-perforation n is given by:

$$N_{O_2} = \frac{D_{O_2-N_2}P}{RT(r_p/2)} \ln\left[\frac{P-p_{out}}{P-p_2}\right] \quad (5)$$

The flux through the cylindrical part is given by the equation:

$$N_{O_2} = \frac{D_{O_2-N_2}P}{RTL} \ln\left[\frac{P-p_{in}}{P-p_{out}}\right] \quad (6)$$

At steady state the flux due to each component will be equal. The unknowns in the three equations (4), (5) and (6) are $P_{in}$ and $P_{out}$. In order to eliminate them, we multiply both sides of equations (4) and (5) by $r_p/2$ and equation (6) by L and add them, which upon rearranging gives equation (7):

$$N_{O_2} = \frac{D_{O_2-N_2}P}{RT(L+r_p)} \ln\left(\frac{P-p_{O_21}}{P-p_{O_22}}\right) \quad (7)$$

This equation is similar to that proposed by Fishman et. al. (1996). The diffusion coefficient can be determined by the equation:

$$\ln D_{if} = \ln a + b\ln(T) - \frac{c}{T} \quad (8)$$

Where a, b and c are constants. The values of the constants for nitrogen-oxygen pair are:
a=1.14×10$^{-7}$ m kPa s$^{-1}$
b=1.724
c=0.0

Using equations (7) and (8), the diffusion through the micro-perforations can be predicted under different conditions. The diffusion coefficient for nitrogen and oxygen at 23° C. is 2.05×10$^{-5}$ m$^2$s$^{-1}$.

Available Mathematical Models

FIG. 6 gives the mathematical models available for predicting the diffusion through microperforations. The data obtained from the static experiments were used for comparing the predicted values by different models.

Statistical Analysis

For the flow-through experiments, each experiment was analyzed at four flow-rates with replicates as blocks. This was essentially a single factor experiment, flow rate being the factor under investigation. The OTR data was subjected to analysis of variance (ANOVA). Balanced ANOVA procedure developed by MINITAB (Minitab, Inc., Pa., 1996) was used to perform ANOVA and an x value of 0.05 used to compare the data.

Diameter and Thickness of the Micro-perforations

FIG. 7 gives the diameter and thickness of the perforations used in these experiments. In order to check the variation in the perforation sizes, diameters of a random sample of micro-perforations were measured.

The mean diameter of the perforations designated as small was 115.9 gm and the mean diameter of the perforations designated as large was 183.5 gm. The data shows a large variation in the diameter for both types of films.

Permeability of Micro-perforated Films Using Flow-through Method

The permeability of the different micro-perforated films as a function of flow rate is shown in FIGS. 8 to 13. The OTR increases with the flow rate with and without pressure adjustments. The flow rate has a significant effect for all the cases considered ($p<0.05$), except for the film with one hole (perforation dia. 96 $\mu$m), when the system is adjusted for pressure ($p>0.05$). This is because of the fact that with increase in flow rate the gradient in concentration decreases. The increase in the OTR without adjustment is more pronounced than that with adjustment. The data also shows that without adjusting for pressure, we get an OTR that is higher than that predicted by Fick's law. This is due to the viscous flow component, which causes this apparent increase in the OTR.

The OTR obtained at 10 cc min$^{-1}$ and adjusted for pressure was used to correlate the flow through OTR with the static OTR since this was the lowest flow-rate at which consistent data was obtained. Preliminary experiments showed that there is a huge variation in the OTR values at flow rates below 10 cc min$^{-1}$. The reason for the variation at low flow rates is that the rate at which the sample is taken out is higher than the flow rate-and causes a vacuum near the film and thus creating a temporary pressure difference. The pressure difference is dependent on the rate at which the sample was drawn from the sampling port, which varied a lot from run to run at low flow rates and thus causing huge variations.

In most cases, we see that the spread in the data is more at higher flow rates. From equation (3.6), we see that the OTR is a product of the flow rate times the oxygen concentration. Hence, a small increase in the oxygen concentration will cause a larger deviation in the OTR at higher flow rates and thus the observed pattern.

Permeability of the Micro-perforated Films Using the Static Method

FIGS. 14 to 19 show the plot of logarithm of ($\Delta c/\Delta c_o$) verses time and also the equation of the regression line and its $R^2$ value. As predicted by equation (2), the plot of In ($\Delta c/\Delta c_o$) verses time is a straight line for all the films tested in this experiment. FIG. 20 gives the oxygen transmission rate obtained for different films.

From the data presented in FIG. 20, the repeatability of the static method is better than the flow through method. The repeatability is better because $\ln(\Delta c/\Delta c_o)$ is not sensitive to small change in the oxygen concentration, while in the case of the flow through method, the multiplication factor is so high that a small change in the oxygen concentration has a large effect on the OTR reading.

As the OTR depends more on the area of the hole, a smaller change in the diameter of a large perforation will have a larger impact on the OTR. This can be seen from the data in FIG. 20. When the diameter changes from 96 $\mu$m to 118 $\mu$m, i. e., a change in 22 $\mu$m, the OTR increases by 40 cc day$^{-1}$. On the other hand when the diameter changes from 160 $\mu$m to 187 $\mu$m, which is an increase of 27 $\mu$m, the OTR increases by 116.5 cc day$^{-1}$. Looking at the large variation in the hole sizes, it can be inferred that it is more safe to use several small micro-perforations than large ones when designing a package as they are less sensitive to size variations as compared to large micro-perforations. Manufacturers, on the other hand, should take care in perfecting the technique for manufacture of the micro-perforated films.

The static method simulates the real package situation, hence it gives a more precise measurement of OTR for the micro-perforated films similar to those seen under real storage conditions. The drawback of the static method is that it is more time consuming as compared to the flow through method. One run on the static method takes about 2 days, as compared to 2 hours on a flow through method. A regression equation was obtained to predict the static OTR ($OTR_{static}$) from the OTR obtained by flow through method when the flow rate is 10 cc min$^{-1}$ and the system is adjusted for pressure difference ($OTR_{flow}$) the number (n) of and the diameter of the micro-perforations (d). The regression equation was obtained by using a log-log transformation of the terms.

$$OTR_{static}=1.195*OTR_{flow}^{0.898}*(nd)^{0.039} R^2=93\% \qquad (9)$$

where $OTR_{static}$ and $OTR_{flow}$ are in cc day$^{-1}$ and d is in $\mu$m.

This equation can be used to predict the OTR values of micro-perforated films under static conditions. Thus one can do the experiments with the flow through method and get the permeability values under static conditions using equation (9). This will reduce the time of experimentation.

Evaluation of different Mathematical Models

The predicted OTR values by the different models in FIG. 6 are given in FIG. 20. The model by Youngquist (1970), which is based on Fick's law, gives higher values than the experimental results. This is expected because there might be a concentration gradient on each side of the holes that is not taken into consideration. Fishman ef al. 's (1996) model has an excellent agreement with the experimental values. The authors approximated the effective length of diffusion from the model presented by Meidner and Mansfield (1968) for computation of stomatal resistance. A derivation of the above model based on Fick's law of diffusion is given in the materials and methods section. The model by Hirata et. al. (1996) under predicts the diffusion values. This equation is actually meant for situation where there is a total pressure difference and thus the reason for the disparity. The model by Fonseca et. al (1996) is an empirical equation and was derived using holes of larger sizes and thickness and thus the reason for the error.

The model for micro-perforation is not valid for perforation of larger sizes (macro-perforations) as seen from the results of Emend et. al. (1991) and Fonseca et. al. (1996). The reason for this being the fact that the assumption 2 used in deriving the equation for micro-perforation is not valid when the diameter of the perforation is large. But the values obtained for the larger perforations are still less than that predicted by Fick's law. In this case too, the concentration gradient does not truncate at either end of the tube. The extension of the gradient can be corrected by a small increase in the actual length of the perforation, similar to those used for two-bulb apparatus for determining the diffusion coefficient for gases. The end correction is given by:

$$L_{eff}=L+aR$$

where $L_{eff}$ is the effective length of the tube, R is its radius and a is a numerical constant whose values depend on the diameter and thickness of the perforation. The value of Cc for micro-perforated films is 1. The value of cc for different diameter and thickness needs to found by empirical methods.

CONCLUSIONS

A workable setup for rapidly measuring the permeability of the micro-perforated films has been developed, using both static and flow-through methods. The static method simulates the normal package conditions and thus the data obtained can be used for designing modified atmosphere packages. The drawback with this method is that it takes a long time to give results, typically two days for one run and a week to run three replicates. This can be overcome if an oxygen or carbon dioxide probe can be inserted into the cell. Research needs to be done on finding a suitable probe, which is stable and gives consistent readings with change in time. The accuracy of the static method can be improved by using a gas- sampling valve at the outlet.

The flow through method is very simple and less time consuming. It takes about two hours to get a set of readings and three replicates can be obtained in half a day. The drawback of the flow through method is that it gives a higher reading than the static method. A regression equation was obtained to get a correlation between the readings obtained by the flow through method with the static method ($R^2$= 93%). These methods can also be used to measure the carbon dioxide permeability.

The water vapor transmission rate (WVTR) through the micro-perforations is another very important parameter, which needs to be known for proper package design for produce. Research needs to be done to find the correlation between the flow through and static methods and conditions for determining WVTR of micro-perforated films.

Five models for predicting the gas exchange through micro-perforation were evaluated. The model by Fishman et. al. (1996), which was the same model derived in these experiments, had a very good agreement with the experimental data. A model was proposed for perforation of any size.

There was a huge variation in the hole sizes, both in the large and small size categories, but thickness did not vary much. The variation in the hole will be detrimental in quality control. The technique for making the micro-perforations needs to be perfected so that-uniform holes can be created in different batches.

The main goal for determining the OTR, or the WVTR, of the film is to have information for the proper design of packaging for produce. Thus, further experiments need to be conducted by packaging produce in micro-perforated films and determining the oxygen concentration inside the package under normal storage conditions, and then check how the experimental data for permeability obtained using the different setups correlates with the data obtained from an actual package.

We claim:

1. A rapid flow-based method to experimentally measure permeability of a first gas in micro-perforated files comprising:

providing a diffusion cell having first and second compartments separated by a test film having micro-perforations, each compartment having an inlet and an outlet for gas flushing;

sweeping the test film with a measured flow of a first gas in said first compartment and with a measured flow of a second gas in said second compartment;

maintaining equal localized pressures on both sides of the micro-perforations;

determining a volume fraction of the first gas at the outlet of said second compartment;

computing an experimental rapid-flow gas transmission rate of the first gas across the test film; and correlating the experimental rapid-flow gas transmission rate with a static gas transmission rate using a number of perforations to calculate a corrected gas transmission rate.

2. The method of claim 1 wherein the step of maintaining equal localized pressures is adjusting a flow rate of the first gas to maintain precise localized equal pressures on both sides of the micro-perforations.

3. The method of claim 1 wherein the step of maintaining equal localized pressures is adjusting a flow rate of the second gas to maintain precise localized equal pressures on both sides of the micro-perforations.

4. The method of claim 1 wherein the step of maintaining equal localized pressures is adjusting flow rates of the first gas and the second gas to maintain precise localized equal pressures on both sides of the micro-perforations.

5. The method of claim 1 wherein the step of correlating includes applying a linear regression to correlate the experimental rapid-flow gas transmission rate with the static gas transmission rate.

6. The method of claim 1 wherein the step of correlating includes using a variable for number of perforations in the film.

7. The method of claim 1 wherein the step of correlating includes using a variable for size of perforations in the film.

8. The method of claim 1 further comprising experimentally determining the static gas transmission rate of the second gas across the test film.

9. The method of claim 1 wherein the first gas is oxygen.

10. The method of claim 1 wherein the second gas is nitrogen.

11. The method of claim 1 wherein the first gas is oxygen and the second gas is nitrogen.

12. The method of claim 1 further comprising packaging a product in a micro-perforated film packaging of a same type as the test film.

13. The method of claim 1 wherein the step of maintaining equal pressures on both sides of the micro-perforations includes adjusting a flow Late of the first gas based on a molecular weight of the first gas.

14. The method of claim 1 wherein the step of maintaining equal pressures on both sides of the micro-perforations includes adjusting a flow rate of the second gas based on a molecular weight of the second gas.

15. The method of claim 1 wherein the step of maintaining equal pressures on both sides of the micro-perforations includes adjusting flow rates of the first gas and the second gas such that a ratio of the first gas flow rate and the second gas flow rate is proportional to a square Toot of a ratio of a second gas molecular weight to a first gas molecular weight.

16. A rapid flow-based method to experimentally measure permeability of a first gas in micro-perforated films comprising:

providing a diffusion cell having first and second compartments separated by a test film having micro-perforations, each compartment having an inlet and an outlet for gas flushing;

sweeping the test film with a measured flow of the first gas in said first compartment and with a measured flow of a second gas in said second compartment;

maintaining equal pressures on both sides of the micro-perforations; determining a volume fraction concentration of the first gas at the outlet of said second compartment;

computing an experimental rapid-flow gas transmission rate of the first gas across the test film; and correlating the experimental rapid-flow gas transmission rate with a static gas transmission rate using a number of micro-perforations and a size of micro-perforations to calculate a corrected gas transmission rate.

17. The method of claim 16 wherein the step of maintaining equal localized pressures is adjusting a flow rate of the first gas to maintain precise localized equal pressures on both sides of the micro-perforations.

18. The method of claim 16 wherein the step of maintaining equal localized pressures is adjusting a flow rate of the second gas to maintain precise localized equal pressures on both sides of the micro-perforations.

19. The method of claim 16 wherein the step of maintaining equal localized pressures is adjusting flow rates of the first gas and the second gas to maintain precise localized equal pressures on both sides of the micro-perforations.

20. The method of claim 16 wherein the step of conelating includes applying a linear regression to correlate the experimental rapid-flow gas transmission rate with the static gas transmission rate.

21. The method of claim 16 further comprising experimentally determining the static gas transmission rate of the second gas across the test film.

22. The method of claim 16 wherein the first gas is oxygen.

23. The method of claim 16 wherein the second gas is nitrogen.

24. The method of claim 16 wherein the first gas is oxygen and the second gas is nitrogen.

25. The method of claim 16 further comprising packaging a product in a micro-perforated film packaging of a same type as the test film.

26. The method of claim 16 wherein the step of maintaining equal pressures on both sides of the micro-perforations includes adjusting a flow rate of the first gas based on a molecular weight of the first gas.

27. The method of claim 16 wherein the step of maintaining equal pressures on both sides of the micro-perforations includes adjusting a flow rate of the second gas based on a molecular weight of the second gas.

28. The method of claim 16 wherein the step of maintaining equal pressures on both sides of the micro-perforations includes adjusting flow rates of the first gas and the second gas such that a ratio of the first gas flow rate and the second gas flow rate are proportional to a square root of a ratio of a second gas molecular weight and a first gas molecular weight.

29. A rapid flow-based method to experimentally measure permeability of a first gas in micro-perforated films comprising:

providing a diffusion cell having first and second compartments separated by a test film having micro-perforations, each compartment having an inlet and an outlet for gas flushing;

sweeping the test film with a measured flow of a first gas in said first compartment and with a measured flow of a second gas in said second compartment;

maintaining equal localized pressures on both sides of the micro-perforations;

determining a volume fraction concentration of the first gas at the outlet of said second compartment;

computing an experimental rapid-flow gas transmission rate of the first gas across the test film; and correlating the experimental rapid-flow gas transmission rate with a static gas transmission rate using a size of perforations to calculate a corrected gas transmission rate.

30. The method of claim 29 wherein the step of maintaining equal localized pressures is adjusting a flow rate of the first gas to maintain precise localized equal pressures on both sides of the micro-perforations.

31. The method of claim 29 wherein the step of maintaining equal localized pressures is adjusting a flow rate of the second gas to maintain precise localized equal pressures on both sides of the micro-perforations.

32. The method of claim 29 wherein the step of maintaining equal localized pressures is adjusting flow rates of the first gas and the second gas to maintain precise localized equal pressures on both sides of the micro-perforations.

33. The method of claim 29 wherein the step of correlating includes applying a linear regression to correlate the experimental rapid-flow gas transmission rate with the static gas transmission rate.

34. The method of claim 29 further comprising experimentally determining the static gas transmission rate of the second gas across the test film.

35. The method of claim 29 wherein the first gas is oxygen.

36. The method of claim 29 wherein the second gas is nitrogen.

37. The method of claim 29 wherein the first gas is oxygen and the second gas is nitrogen.

38. The method of claim 29 further comprising packaging a product in a micro-perforated film packaging of a same type as the test film.

39. The method of claim 29 wherein the step of maintaining equal pressures on both sides of the micro-perforations includes adjusting a flow rate of the first gas based on a molecular weight of the first gas.

40. The method of claim 29 wherein the step of maintaining equal pressures on both sides of the microperforations includes adjusting a flow rate of the second gas based on a molecular weight of the second gas.

41. The method of claim 29 wherein the step of maintaining equal pressures on both sides of the micro-perforations includes adjusting flow rates of the first gas and the second gas such that a ratio of the first gas flow rate and the second gas flow rate is proportional to a square root of a ratio of a second gas molecular weight to a first gas molecular weight.

* * * * *